(12) United States Patent
Newman et al.

(10) Patent No.: US 10,962,762 B2
(45) Date of Patent: Mar. 30, 2021

(54) REMOTE INSPECTION DEVICE

(71) Applicant: Inspectron, Inc., Novi, MI (US)

(72) Inventors: Tye L. Newman, Howell, MI (US); Brent F. Lyons, Howell, MI (US)

(73) Assignee: INSPECTRON, INC., Novi, MI (US)

(*) Notice: Subject to any disclaimer, the term of this patent is extended or adjusted under 35 U.S.C. 154(b) by 0 days.

(21) Appl. No.: 16/427,528

(22) Filed: May 31, 2019

(65) Prior Publication Data

US 2019/0369381 A1 Dec. 5, 2019

Related U.S. Application Data

(60) Provisional application No. 62/679,090, filed on Jun. 1, 2018, provisional application No. 62/728,202, filed on Sep. 7, 2018.

(51) Int. Cl.
| | | |
|---|---|---|
| *G02B 23/24* | (2006.01) | |
| *H01B 7/04* | (2006.01) | |
| *H04N 5/225* | (2006.01) | |
| *A61B 1/00* | (2006.01) | |
| *A61B 1/05* | (2006.01) | |
| *A61B 1/005* | (2006.01) | |
| *G01N 21/954* | (2006.01) | |

(52) U.S. Cl.
CPC .......... *G02B 23/2484* (2013.01); *A61B 1/005* (2013.01); *A61B 1/0008* (2013.01); *A61B 1/00066* (2013.01); *A61B 1/05* (2013.01); *H01B 7/041* (2013.01); *H04N 5/2252* (2013.01); *G01N 21/954* (2013.01); *H04N 2005/2255* (2013.01)

(58) Field of Classification Search
CPC ............... G02B 23/24; G02B 23/2407; G02B 23/2415; G02B 23/2423; G02B 23/243; G02B 23/2446; G02B 23/2453; G02B 23/2461; G02B 23/2469; G02B 23/2476; G02B 23/2484; G02B 23/26; A61B 1/00; A61B 1/00002; A61B 1/00064; A61B 1/00066; A61B 1/00071; A61B 1/0008; A61B 1/00131; A61B 1/00133; A61B 1/0037; A61B 1/00147; A61B 1/00149; A61B 1/00154; A61B 1/0016; A61B 1/00163; A61B 1/005; A61B 1/0057; A61B 1/008; A61B 1/01; A61B 1/012; A61B 1/0125; A61B 1/018; A61B 1/04; A61B 1/05; H01B 7/041; H01B 7/048; H04N 5/2251; H04N 5/2252; G01N 21/954; G01N 2021/9542; G01N 2021/9544; G01N 2021/9546; G06T 7/0004; G06T 7/0012
USPC .......................................... 356/241.1–241.6
See application file for complete search history.

(56) References Cited

U.S. PATENT DOCUMENTS

| | | | | |
|---|---|---|---|---|
| 4,750,475 A | * | 6/1988 | Yoshihashi | ............ A61B 10/04 600/131 |
| 7,581,988 B2 | * | 9/2009 | Boehnlein | .......... A61B 1/00052 439/585 |

(Continued)

*Primary Examiner* — Gordon J Stock, Jr.
(74) *Attorney, Agent, or Firm* — Dickinson Wright PLLC

(57) ABSTRACT

A portable inspection unit is provided. The portable inspection unit may include a unit body, a flexible cable, and an imager housing. The flexible cable may extend from the unit body and the imager housing may be disposed at a distal end of the flexible cable. The portable inspection unit may include a grasper that extends and retracts from the imager housing.

14 Claims, 17 Drawing Sheets

(56) References Cited

U.S. PATENT DOCUMENTS

| | | | |
|---|---|---|---|
| 7,842,028 B2 * | 11/2010 | Lee | A61B 17/0218 606/1 |
| 2008/0308602 A1 * | 12/2008 | Timm | A61B 17/07207 227/175.1 |
| 2009/0306470 A1 * | 12/2009 | Karasawa | A61B 1/313 600/103 |
| 2010/0277578 A1 * | 11/2010 | Mitchell | H04N 5/2251 348/61 |
| 2011/0009694 A1 * | 1/2011 | Schultz | A61B 1/00105 600/109 |
| 2014/0192179 A1 * | 7/2014 | Lyons | H04N 7/183 348/84 |
| 2014/0296866 A1 * | 10/2014 | Salman | A61B 1/015 606/109 |
| 2018/0309908 A1 * | 10/2018 | Matthison-Hansen | H04N 5/2251 |

* cited by examiner

REMOTE INSPECTION DEVICE

CROSS REFERENCE TO RELATED APPLICATIONS

This application claims the benefit of U.S. Provisional Patent Application No. 62/679,090 filed Jun. 1, 2018 and U.S. Provisional Application No. 62/728,202, filed Sep. 7, 2018, the content of which is hereby incorporated by reference in its entirety.

FIELD OF THE INVENTION

The present disclosure relates generally to a portable inspection unit and more specifically to a portable inspection unit with a grasper.

BACKGROUND

Borescopes and video scopes for inspecting visually obscured locations are typically tailored for particular applications. For instance, some borescopes have been tailored for use by plumbers to inspect pipes and drains. Likewise, other types of borescopes have been tailored for use by mechanics to inspect interior compartments of machinery being repaired. Special features and functions associated with these applications have driven up the cost for these types of devices. This disclosure provides for an improved borescope having the added flexibility to improve functionality and maintain reduced cost. The statements in this section merely provide background information related to the present disclosure.

DETAILED DESCRIPTION

Figure 1:
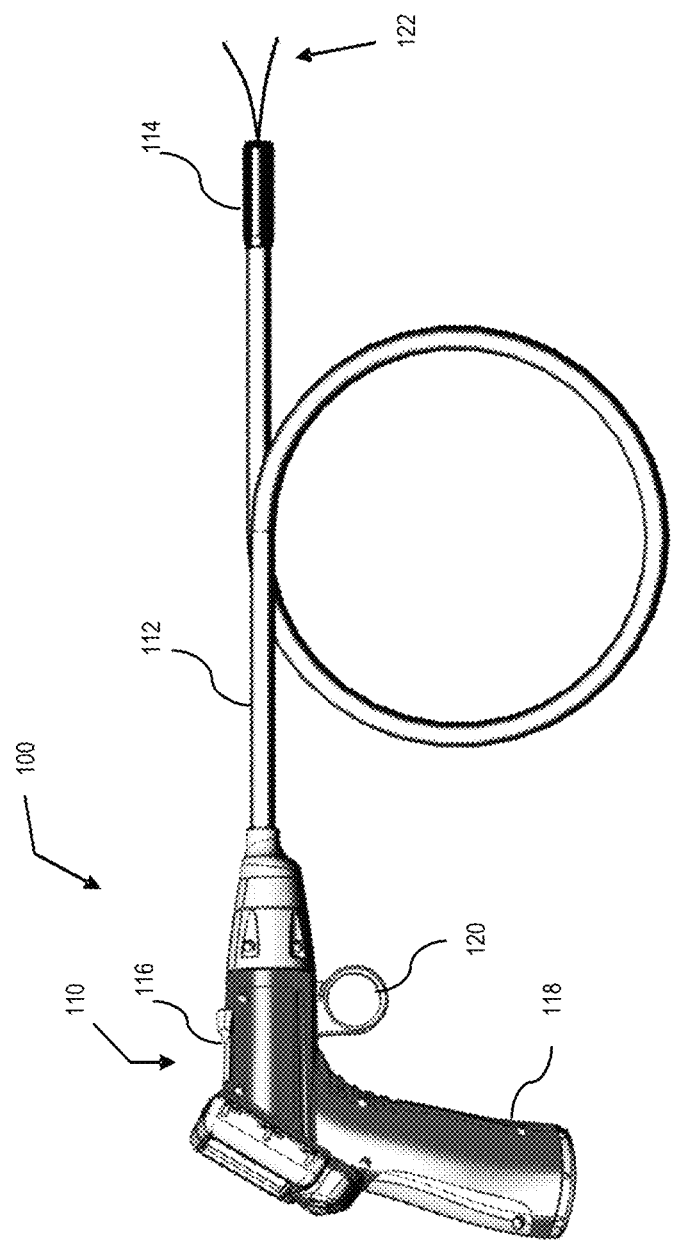
FIG. 1 is a side view of an implementation of a portable inspection unit in accordance with the disclosure.

Referring to FIG. 1, an exemplary implementation of a portable inspection unit 100 is illustrated in accordance with the disclosure. The portable inspection unit 100 may generally comprise three primary components: unit body 110, flexible cable 112 and an imager housing 114. The flexible cable 112 may extend from a distal end portion of the unit body 110 to a proximal end portion of the imager housing and may further provide for mechanical connection and electrical communication between the imager housing 114 and the unit body 110. The portable inspection unit disclosed herein provides for improved adaptability in a range of applications. As discussed in further detail throughout this disclosure, the portable inspection unit and its various components provide for an adaptable inspection tool that may be used for viewing and accessing obscured locations with various accessories.

The unit body may further comprise a surface portion having an access port 116, a handle 118, and a trigger mechanism 120. The unit body may provide for an ergonomic design allowing for ease of access to the trigger mechanism and single handed operation. In this implementation, the portable inspection unit may further comprise a grasper accessory (grasper) 122 extending from the distal end portion of the imager housing 114. The grasper 122 may comprise a plurality of tines suitable for grasping various objects that may be encountered during operation of the portable inspection unit. The grasper 122 may generally be incorporated in the inspection unit by passing through an elongated passageway (e.g. a tube) extending from the unit body, through the flexible cable and passing through the imager housing. The grasper may further be configured to connect to the trigger mechanism of the unit body to engage actuation of the grasper. Though the grasper accessory is demonstrated in this implementation, the internal passageway may be configured to receive various accessories compatible with portable inspection unit for improved adaptation and ease of serviceability.

Figure 2:
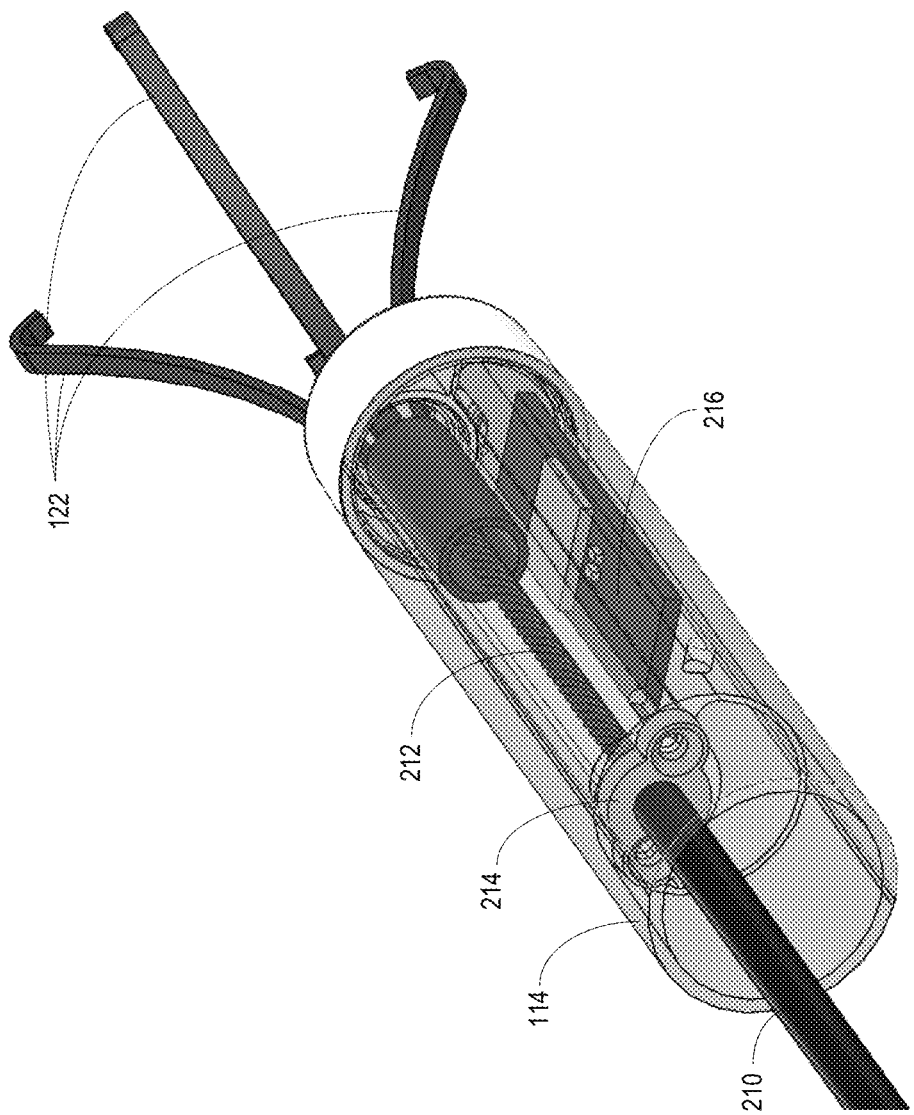
FIG. 2 is a transparent view of an imager housing of the portable inspection unit.

Referring now to FIG. 2, the imager housing 114 is shown receiving an actuating device in the form of the grasper 122. The grasper 122 shown may comprise a plurality of tines. In one implementation the grasper 122 comprises three tines extending from the internal passageway 210. The grasper 122 may include a grasper cable 212 that extends from the unit body 110 through the internal passageway 210 inside the flexible cable 112 and exits the distal end of the imager housing 114. The tines may further extend outward along a smooth curve and may also be evenly spaced radially about a longitudinal axis of the imager housing 114. Each of the tines may further comprise at least one barb proximate to a distal end portion. In some implementations, each barb may comprise a single point, while in others, a plurality of raised ridges may be disposed at the distal end of each tine to form a plurality of barbs.

At a proximal end portion, each of the tines may merge together to form a single draw wire 212. The draw wire 212 may be disposed in the internal passageway 210 passing through the imager housing 114 and the length of the flexible cable 112 into the unit body 110. Once inside the unit body 110, the draw wire 212 may extend along a channel portion of the actuating unit to the distal end where it may be constrained or attached to the drive unit. Upon actuation of the drive assembly, the draw wire 212 may be extended from the unit body 110 by the actuating unit. Resulting from the motion of the actuating unit, the draw wire 212 may extend further into the imager housing 114 causing the distal end portions of the tines comprising the barbs to extend from the end of the imager housing 114 and diverge. Through this motion, an object near the distal end portion may be engaged and held by the tines of the grasper. This functionality may allow for the removal of various objects that may be viewed be the imager unit in locations otherwise obscured from view. In some cases an alternate grasping unit may also be used for placement of objects in confined areas or areas obscured from view.

To ensure that a variety of objects may be engaged by with the grasper are the plurality of tines may be evenly spaced and diverge outward radially in a smoothed curved path or may be configured for other applications requiring other spacing. In other implementations the tines may be magnetized to allow for the capture of ferromagnetic materials.

The internal passageway 210 may be attached to the flexible cable 112 (e.g. through the imager housing 114) such that the location for the distal end of the internal passageway 210 remains constant relative to the distal end of the flexible cable 112. Accordingly, distal end of internal passageway 210 may be fixed to the imager housing 114 (e.g. through adhesive, a collar, or a clamp 214) such that the location for the distal end of the internal passageway 210 remains constant to the distal end of the flexible cable 112 regardless of bending or coiling of the flexible cable 112. This keeps the length of the internal passageway along the grasper cable 212 fixed relative to the length of the flexible cable 112 along the grasper cable 212.

The imager housing 114 may also contain electronics 216 such as an imager, lighting, lighting control, communication, and power circuitry. Power and communication may be provided to the electronics 216 through wires that extend through the flexible cable 112 from the unit body 110.

Figure 3:
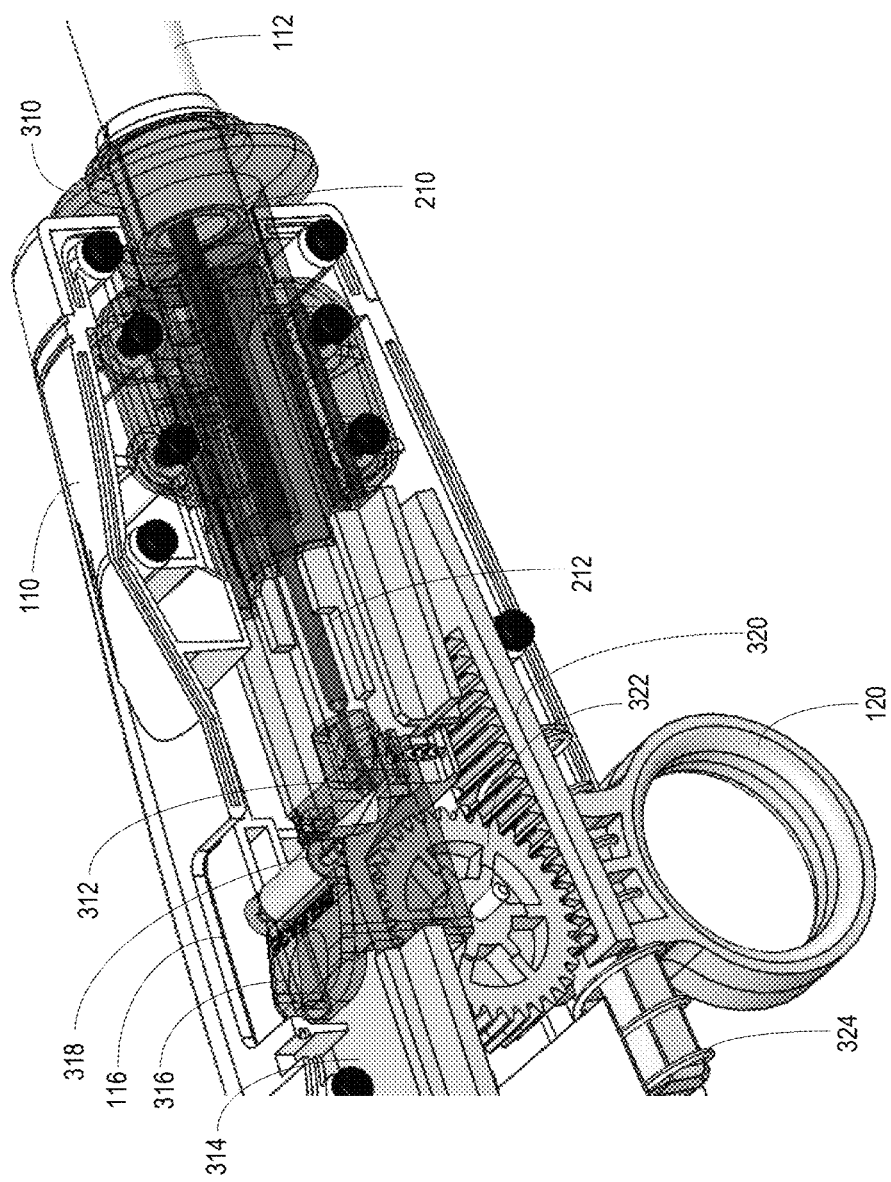
FIG. 3 is a cross-sectional perspective view of the unit body of the portable inspection unit in accordance with the disclosure.
Figure 4:
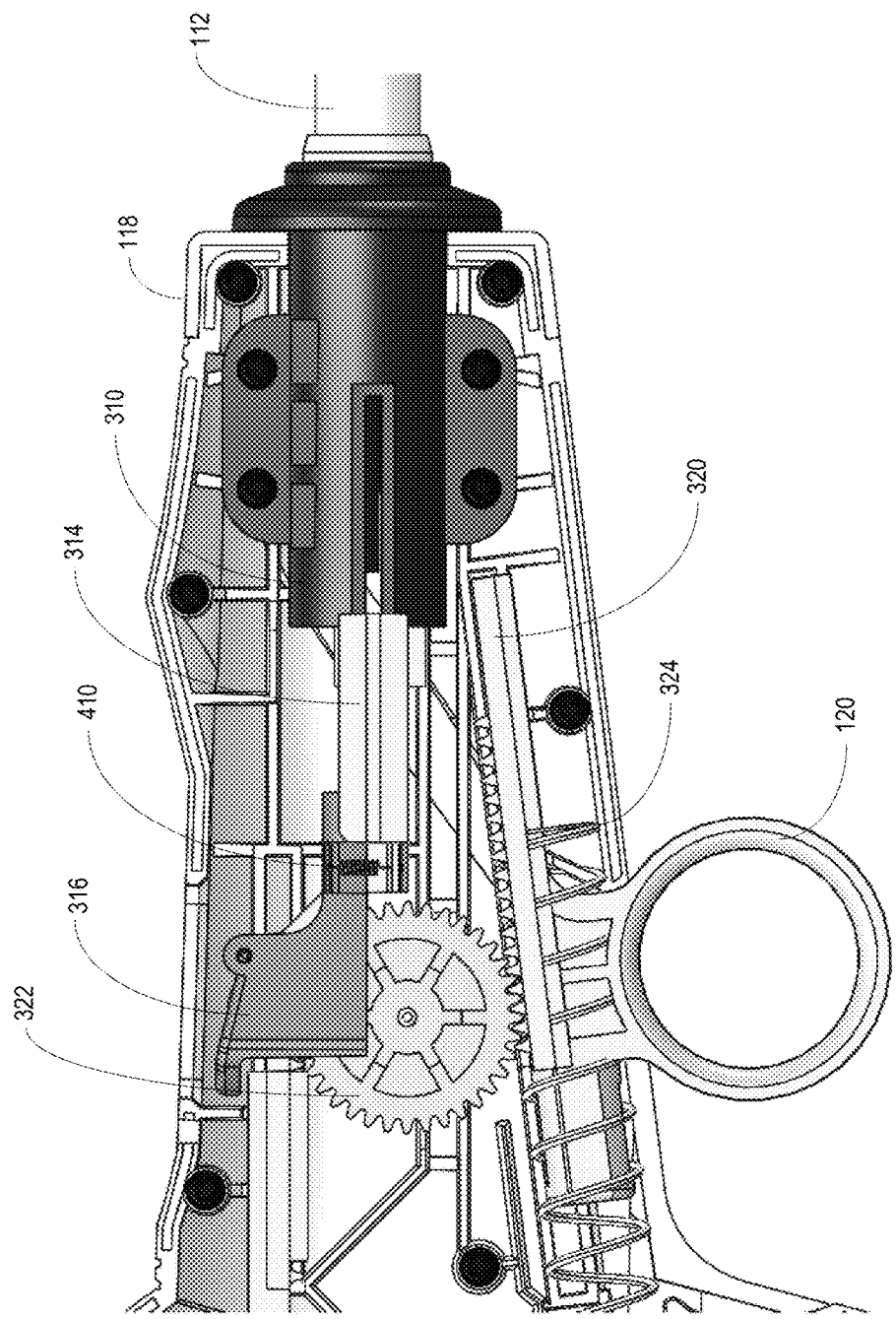
FIG. 4 is a cross-sectional side view of the unit body of the portable inspection unit.

Referring now to FIG. 3 and FIG. 4, a partial cross-sectional view of the unit body 110. The trigger mechanism 120 may define an engaging portion of a drive assembly. The drive assembly may further comprise a drive unit 320, an actuating unit 314, and at least one gear 322. The drive unit 320 may be configured such that upon engagement of the trigger mechanism 120, the drive unit 320 may be drawn toward the handle of the body unit 110, and the at least one gear 322 may be engaged by a drive rack portion of the drive unit 320. Actuation of the drive unit 320 may cause rotation in the at least one gear 322 and further engage an actuating rack of an actuating unit 314. The actuating unit 314 may engage the grasper 122 (e.g. the proximal end of the grasper cable 212). Accordingly, as the trigger is moved forward or backward the tines of the grasper 122 are extended or retracted from the end of the imager housing. A trigger spring 324 may bias the trigger 120 in one direction such that the grasper 122 is in a retracted position.

The body unit 110 may include a lever 316 configured to retain or release the proximal end for the grasper cable 212 from engagement with the actuating unit 314. The lever 316 may extend outside from the outer surface of the body unit 316 through the port 116. This may improve accessibility to the lever 316. Alternatively, the lever 316 may be accessed by reaching through the port 116. The lever 316 may rotate on a pivot 318, such that when the accessible portion of the lever 316 is depressed an arm on an opposite side of the pivot 318 is lifted to release the grasper 122 from being engaged by the actuating unit 314. A lever spring 410 may bias the lever 316 into a position that retains engagement of the grasper 122 with the actuating unit 314.

The grasper cable 212 may attach to the drive unit 314. As such, the grasper cable 212 may be extended or retracted as the drive unit 314 moves distally or proximally, respectively. The grasper cable 212 may extend from the drive unit 314 through the internal passageway 210 inside the flexible cable 112 to the imager housing 114.

The internal passageway 210 may be attached to the flexible cable 112 (e.g. through the body unit 110) such that the location for the proximal end of the internal passageway 210 remains constant to the proximal end of the flexible cable 112. Accordingly, proximal end of internal passageway 210 may be fixed to the body unit 110 (e.g. through adhesive, a collar 310, or a clamp) such that the location for the proximal end of the internal passageway 210 remains constant to the proximal end of the flexible cable 112 regardless of bending or coiling of the flexible cable 112. This keeps the length of the internal passageway 210 along the grasper cable 212 fixed relative to the length of the flexible cable 112 along the grasper cable 212.

Figure 5:
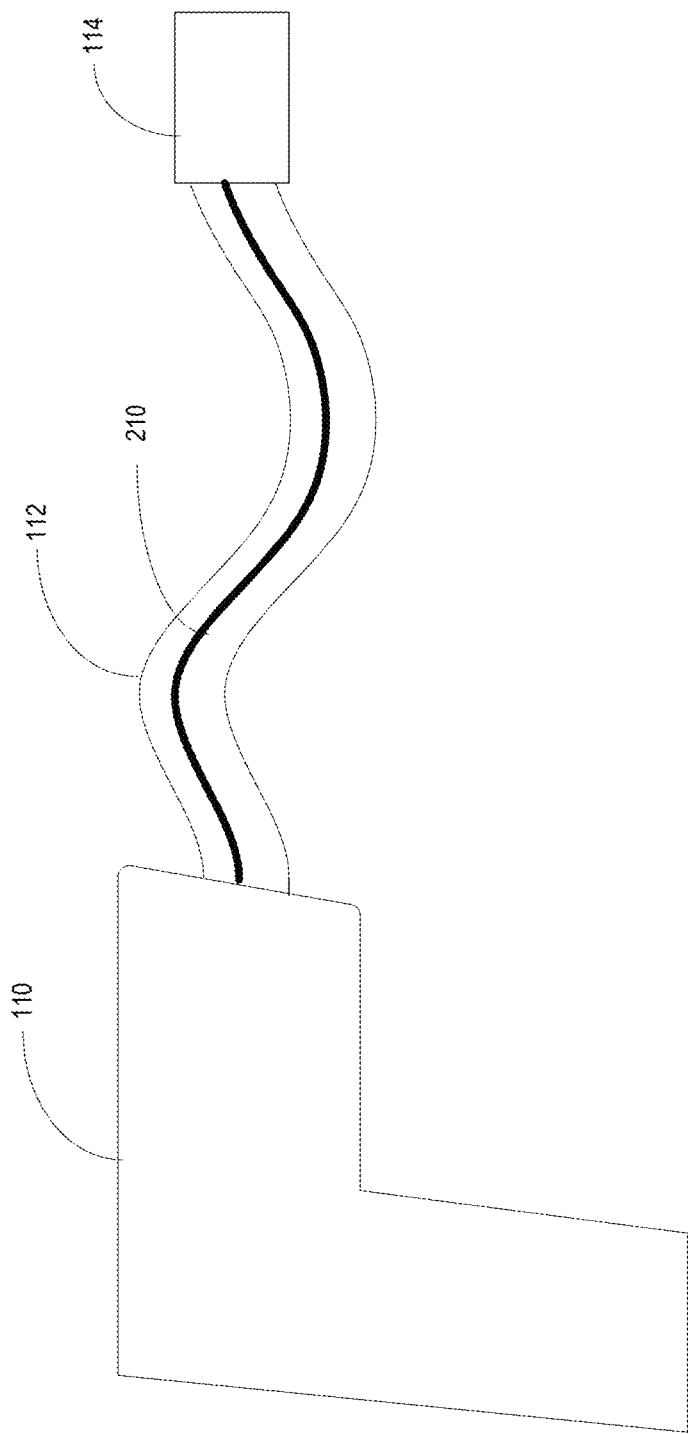
FIG. 5 is a side view of portable inspection unit where the internal passageway is fixed on both ends.

FIG. 5 is a schematic view of a portable inspection unit illustrating one scenario where the internal passageway 210 is fixed on both ends relative to the flexible cable 112. In this instance, the distance spanned between the unit body 110 and the imager housing 114 by the internal passageway 210 is equal to the distance spanned by the flexible cable 112. The grasper cable 212 closely follows the internal passageway 210 and may extend a desired distance into the imager housing 114. In this scenario, the tines of the grasper 122 may fully extend past the end of the imager housing 114 when the trigger 120 is in the extended position and the tines may be fully retracted within the imager housing 114 when the trigger 120 is in the retracted position.

Figure 6:
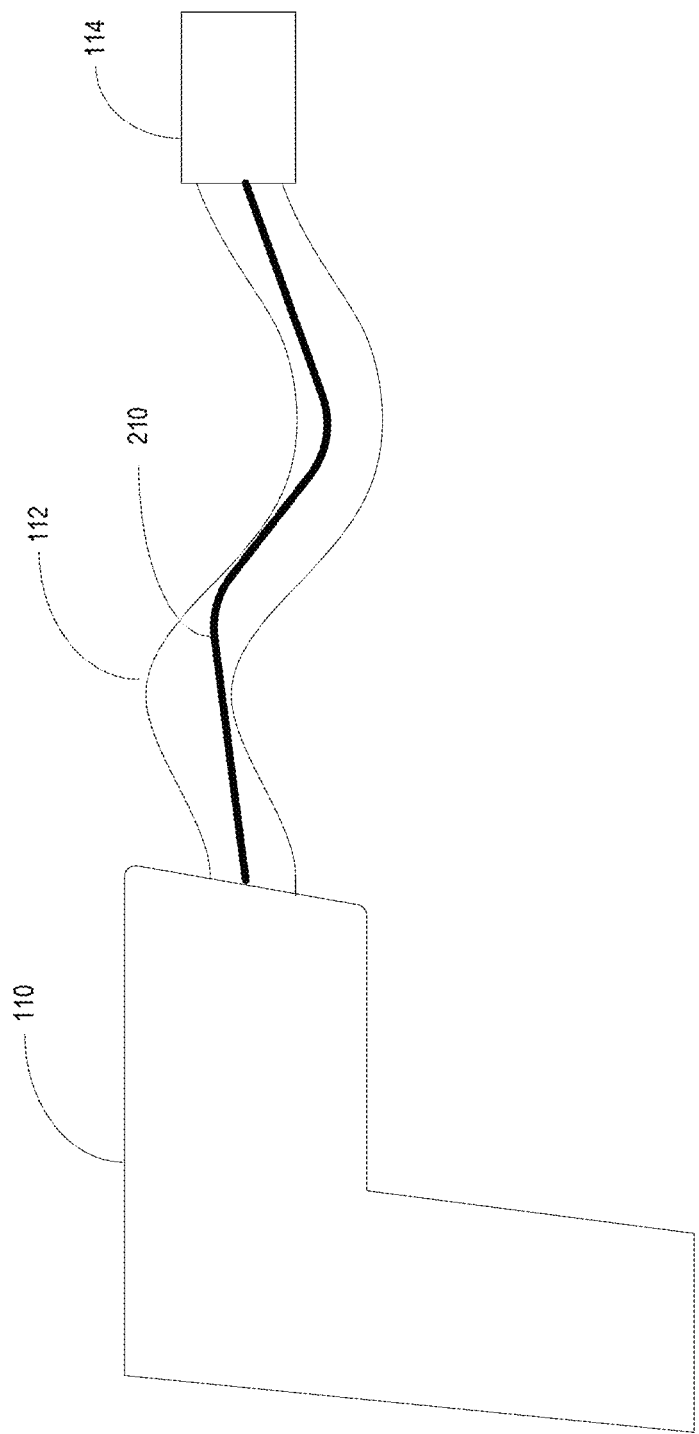
FIG. 6 is a side view of the portable inspection unit illustrating the internal passageway having a shorter path than the flexible cable.

FIG. 6 is a schematic view of a portable inspection unit illustrating one scenario where the internal passageway 210 is not fixed on both ends relative to the flexible cable 112. In this instance, the distance spanned between the unit body 110 and the imager housing 114 by the internal passageway 210 is less than the distance spanned by the flexible cable 112. However, the system would typically be designed to have the distance be the same between internal passageway 210 and flexible cable 112, for example when the flexible cable 112 and the internal passageway 210 straight (or at least follow parallel paths). Accordingly, the grasper cable 212 closely follows the internal passageway 210 and may extend further into the imager housing 114 than planned with the trigger 120 in the retracted position. In some scenarios, the tines of the grasper 122 may extend past the end of the imager housing 114 even though the trigger 120 is in the retracted position. A common situation where this may occur is when a portion of the flexible cable 112 is coiled.

Figure 7:
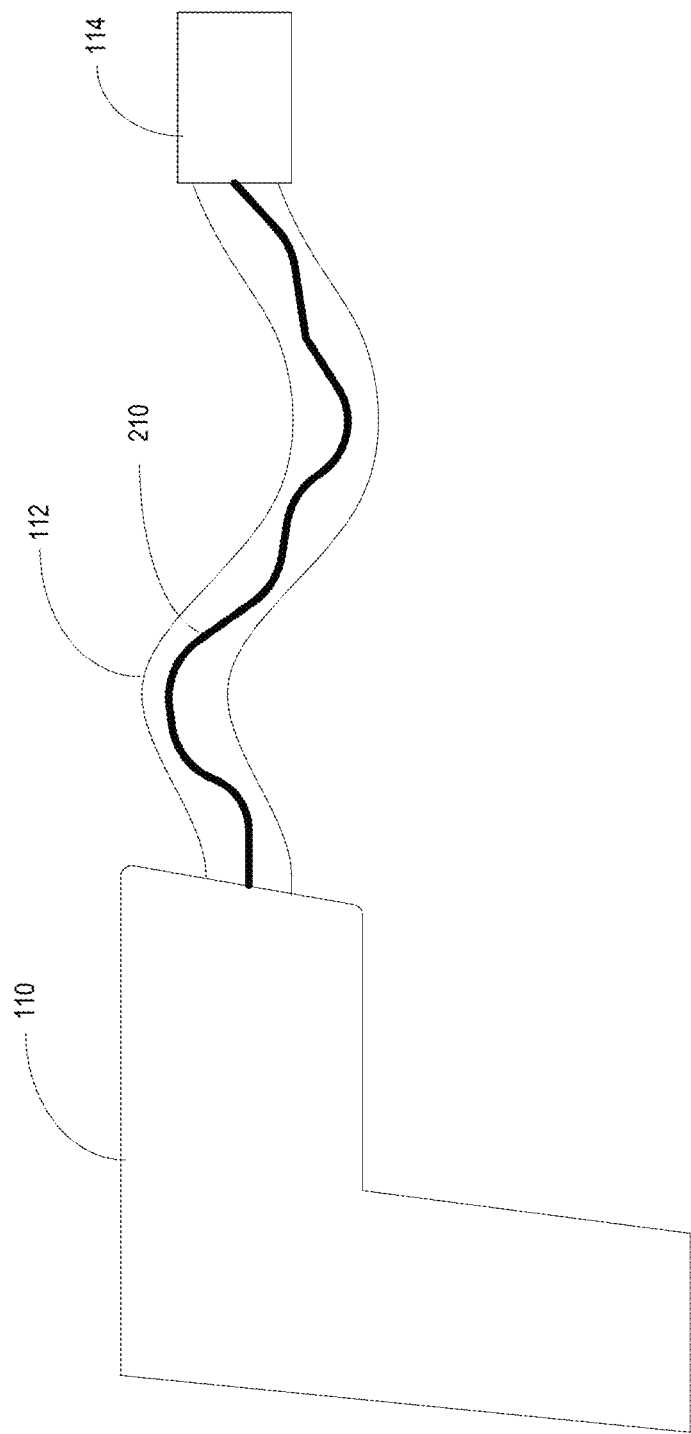
FIG. 7 is a side view of the portable inspection unit illustrating the internal passageway having a longer path than the flexible cable.

FIG. 7 is a schematic view of a portable inspection unit illustrating another scenario where the internal passageway 210 is not fixed on both ends relative to the flexible cable 112. In this instance, the distance spanned between the unit body 110 and the imager housing 114 by the internal passageway 210 is more than the distance spanned by the flexible cable 112. However, the system would typically be designed to have the distance be the same between internal passageway 210 and flexible cable 112, for example when the flexible cable 112 and the internal passageway 210 follow parallel paths. The grasper cable 212 closely follows the internal passageway 210 and may extend into the imager housing 114 less than planned with the trigger 120 in the retracted position. In some scenarios, the tines of the grasper 122 may not fully extend past the end of the imager housing 114 even though the trigger 120 is in the extended position.

Figure 8A:
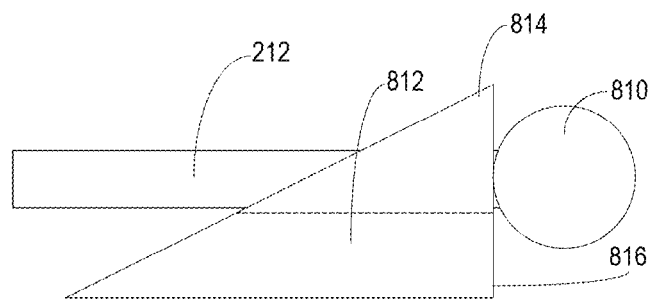
FIG. 8A is a side view of one implementation of a retaining mechanism.
Figure 8B:
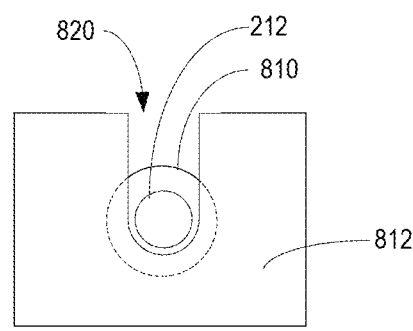
FIG. 8B is a front view of the retaining mechanism in FIG. 8A.

FIG. 8A is a side view of one implementation of a retaining mechanism 812 and FIG. 8b is a front view of the retaining mechanism 812. The retaining mechanism 812 may be formed as part of or fixed to the drive unit 314. The retaining mechanism 812 may engage a feature 810 on the proximal end of the grasper cable 212. The feature 810 may be a flat disk, a crimp, or a ball. The feature 810 may have a width greater than the cable width of the grasper cable 212. The retaining mechanism 812 may have a front surface 814 that may be sloped relative to the central axis 818 of the internal passageway 210 (e.g. the central axis of the grasper cable 212). As the feature 810 is pushed toward the retaining mechanism 812, the feature may ride up the slope of the front surface 812. As the feature 810 is pushed beyond the back edge of the front surface 814, the grasper cable 212 may fall into a slot 820 in the retaining mechanism 812.

The slot 820 may extend from the front surface 814 of the retaining mechanism 812 to the back surface 816 of the retaining mechanism 812 (e.g. running along the length direction of the grasper cable 212. The tension in the grasper cable 212 (and/or gravity) may force the grasper cable 212 down into the slot 820. The feature 810 may have a width greater than the width of the slot 820. As such, the feature 810 may be forced against the back surface 816 and engaged to move in fixed relation to the retaining mechanism 812.

The slot 820 may be aligned with central axis of the grasper cable 212 and the feature 810 may have a width greater than a width of the slot 820. The back surface 816 may substantially perpendicular to the central axis of the grasper cable 212.

Figure 9A:
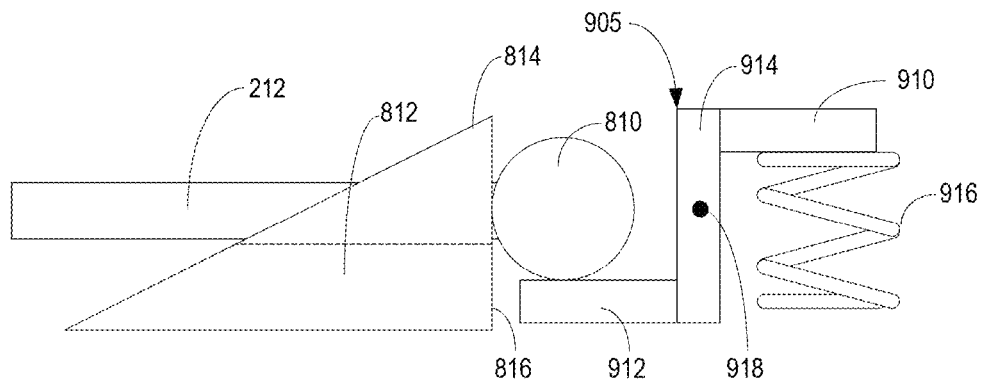
FIG. 9A is a side view of one implementation of a retaining mechanism and a lever.

FIG. 9A is side view of a retaining mechanism 812 and a lever 905. The lever 905 may be positioned such that a first arm 910 of the lever 905 is presented to the user for being pressed in a downward motion to release the feature 810 from engagement with the retaining mechanism 812. As the first arm 910 is pressed downward, a connecting portion 914 of the lever 905 may rotate about a pivot 918. The rotating motion of the connecting portion 914, may cause the second arm 912 to move upward. As the second arm 912 moves upward it may force the feature 810 upward over the edge of the first surface 814 of the retaining mechanism 812. This allows the grasper cable 212 to be pulled forward moving the feature 810 down the slope and away from the retaining mechanism 812. A spring 916 may bias the first arm 910 upward so that the default position would keep the feature 810 in engagement with the retaining mechanism 812.

Figure 9B:
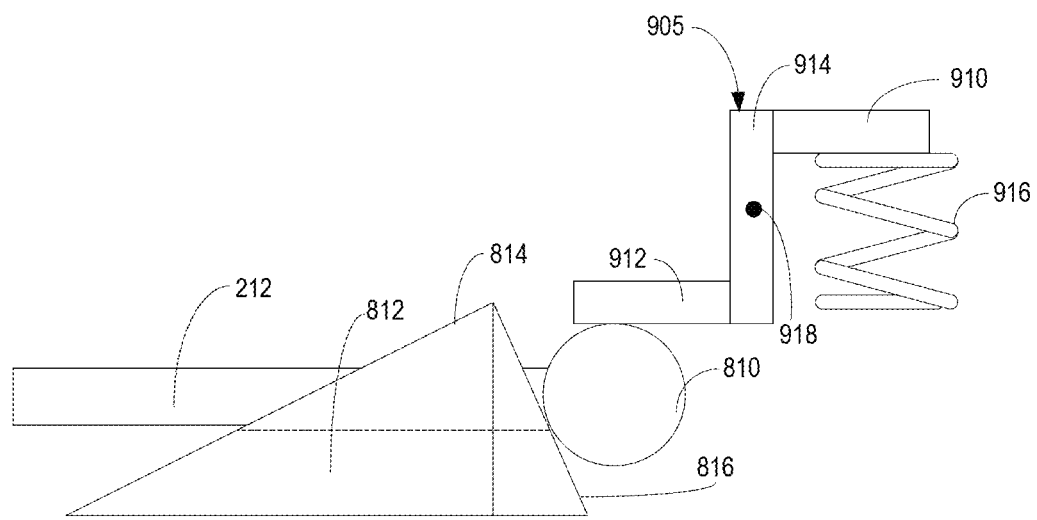
FIG. 9B is a side view of another implementation of a retaining mechanism and a lever.

FIG. 9B is side view of a retaining mechanism 812 and another lever 905. The lever 905 may be positioned such that a first arm 910 of the lever 905 is presented to the user for being pressed in a downward motion to release the feature 810 from engagement with the retaining mechanism 812. As the first arm 910 is pressed downward, a connecting portion 914 of the lever 905 may rotate about a pivot 918. The rotating motion of the connecting portion 914, may cause the second arm 912 to move upward. As the second arm 912 moves upward it may force the feature 810 upward over the edge of the first surface 814 of the retaining mechanism 812. This allows the grasper cable 212 to be pulled forward moving the feature 810 down the slope and away from the retaining mechanism 812. A spring 916 may bias the first arm 910 upward so that the default position would keep the feature 810 in engagement with the retaining mechanism 812.

The slot 820 may be aligned with central axis of the grasper cable 212 and the feature 810 may have a width greater than a width of the slot 820. The back surface 816 may sloped to the central axis of the grasper cable 212, for example in an opposite direction to the front surface 814.

It is also contemplated that the lever 905 could have two arms opposite the first arm 910, for example, one arm below the feature 810 as shown in FIG. 9A and another arm above the feature 810 as shown in FIG. 9B.

Figure 10:
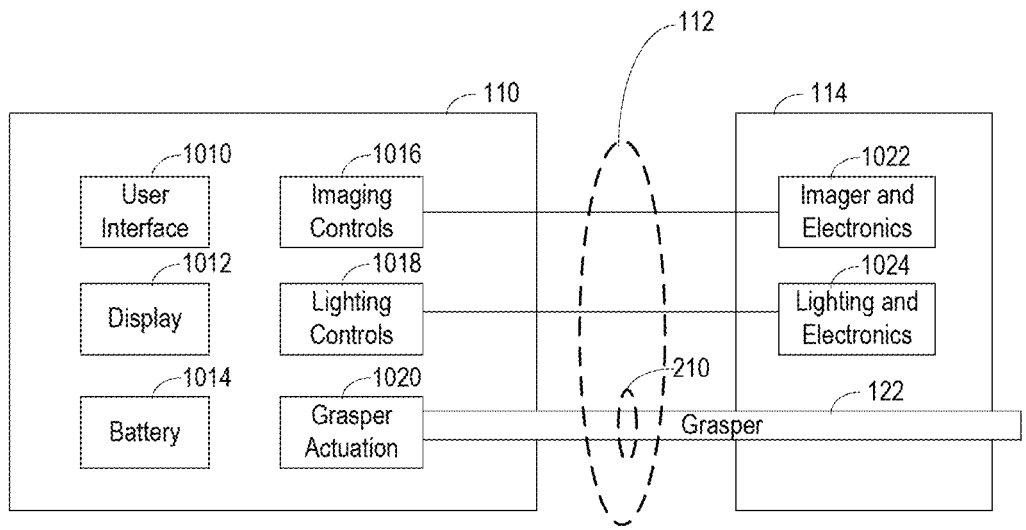
FIG. 10 is a block diagram illustrating the electronics of the portable inspection unit.

Referring to FIG. 10, a block diagram of an implementation of the portable inspection unit is shown. The portable inspection unit may include user interface 1010, a display 1012, and a power supply, for example one or more batteries 1014, inside the body unit 110. Additionally, the body unit 110 may include imaging controls 1016 and lighting controls 1018. The body unit 110 may house a grasper actuation unit 1020, for example, the drive unit, gears, and trigger, in FIG. 3. A grasper 122 may extend from the body unit 110 to the imager housing 114 through internal passageway 210 (such as a tube) in the flexible cable 112. The internal passageway 210 may be a tube that is only slightly larger diameter than the grasper cable. Further, the tube may be fixed to both ends of the flexible cable 112 (either directly or through the imager housing 114 and/or the body unit 110). Additionally, communication and power lines may be connected from the imaging controls 1016 and lighting controls 1018 to an imager 1022 and lighting 1024 through the flexible cable, but not through the internal passageway 210 for the grasper 122.

Figure 11:
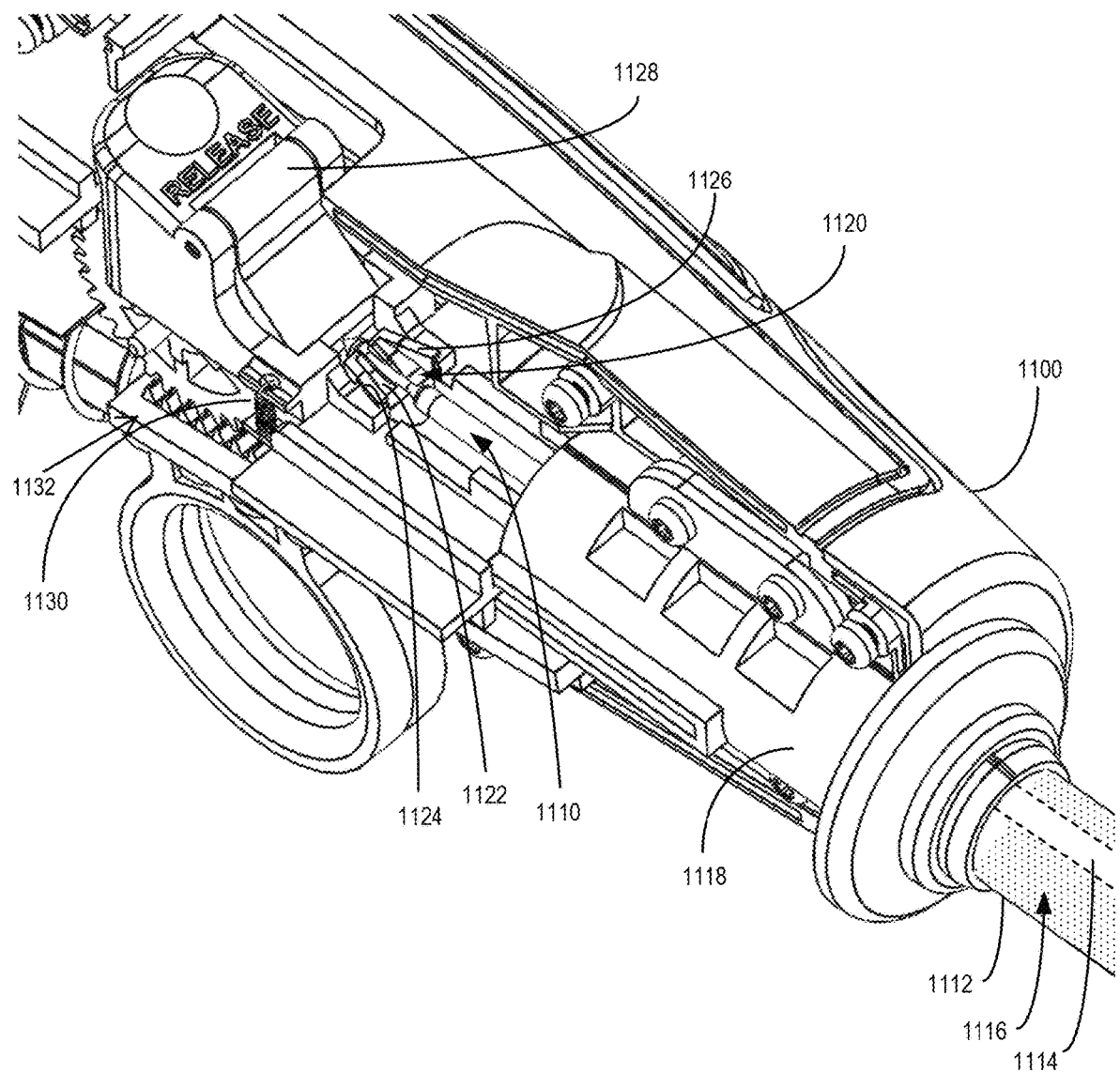
FIG. 11 is a partial cross-sectional view of one implementation of the unit body.

FIG. 11 is a partial cross-sectional view of one implementation of a unit body as discussed elsewhere in this application. The body unit 1100 may include a lever 1128 configured to retain or release the proximal end of the grasper cable 1110 from engagement with the retaining mechanism 1120. The lever 1128 may extend outside the outer surface of the body unit 1100 through a port. Alternatively, the lever 1128 may be accessed by reaching through the port. The lever 1128 may rotate on a pivot, such that when the accessible portion of the lever 1128 is depressed an arm on an opposite side of the pivot is lifted to release the proximal end of the grasper cable 1110 from being engaged by the retaining mechanism 1120. A lever spring 1130 may bias the lever 1128 into a position where the grasper cable 1110 is engaged the retaining mechanism 1120.

The retaining mechanism 1120 may include a surface 1122 angled (e.g. between 30 to 60 degrees) relative to the longitudinal axis of the grasper cable 1110 to divert an end portion (e.g. a ball or conical shape) allowing the cable to rest in a slot in the retaining mechanism 1120 while the end portion is engaged by the retaining mechanism 1120. Further, the retaining mechanism 1120 may include a lip 1124 on the left and a lip 1126 on the right side to guide the end portion toward the slot in the middle of the surface 1122.

The retaining mechanism 1120 may attach to the drive unit 1132. As such, the grasper cable 1110 may be extended or retracted as the drive unit 1132 moves distally or proximally, respectively. The grasper cable 1110 may extend from the drive unit 1132 through the tube 1114 inside the flexible cable 1112 to the imager housing.

The tube 1114 may be attached to the flexible cable 1112 (e.g. through the body unit 1100) such that the location for the proximal end of the tube 1114 remains constant to the proximal end of the flexible cable 1112. Accordingly, proximal end of tube 1114 may be fixed to the body unit 1100 (e.g. through adhesive, a collar 1118, or a clamp) such that the location for the proximal end of the tube 1114 remains constant to the proximal end of the flexible cable 1112 regardless of bending or coiling of the flexible cable 1112. This keeps the length of the tube 1114 along the grasper cable 1110 fixed relative to the length of the flexible cable 1112 along the grasper cable 1110.

A filling material 1116 may be located between an inner wall of the flexible cable 1112 and an outer wall of the tube 1114. The filing material 1116 may surround the tube 1114 between an inner wall of the flexible cable 1112 and an outer wall of the tube 1114 fixing a distance between the inner wall of the flexible cable 1112 and the outer wall of the tube 1114. The filing material 1116 may surround the tube 1114 along at least 50% of the length of the tube 1114. The density of the filing material 1116 may be at least 0.03 g/cm$^3$ or may be less than 1.2 g/cm$^3$ or between 0.03 g/cm$^3$ and 1.2 g/cm$^3$. The filing material 1116 may comprise a nylon, foam, or cotton material.

Figure 12:
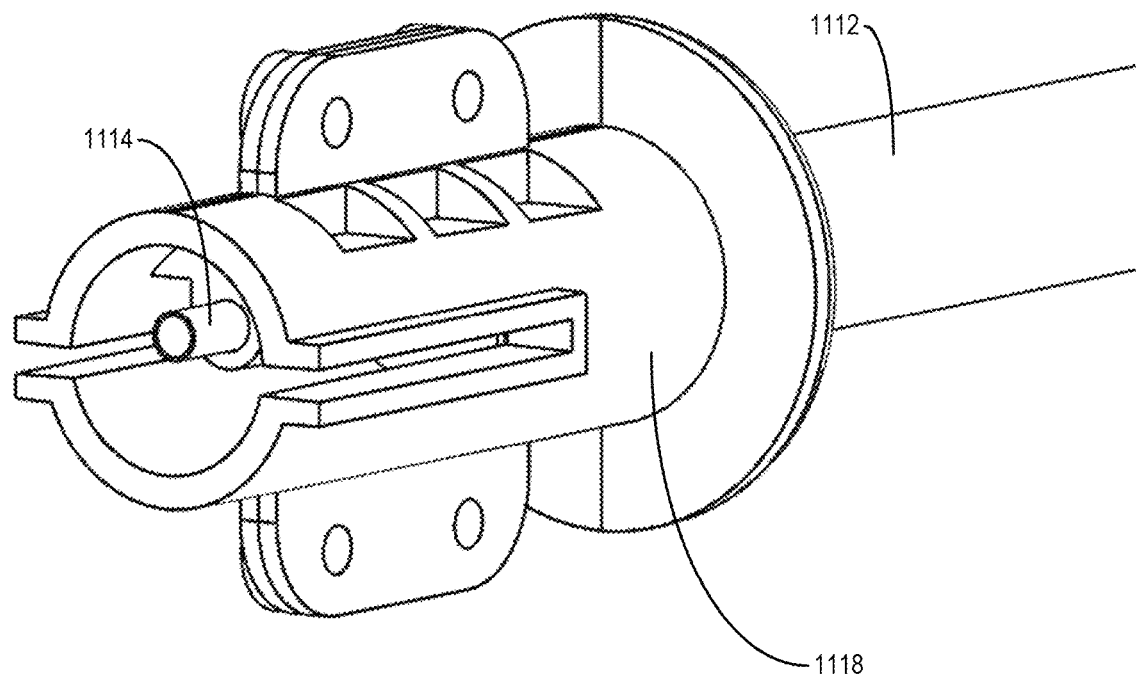
FIG. 12 is an end view of the tube attachment to a collar of the body unit.

FIG. 12 is an end view of the tube 1114 where it is attached to the collar 1118. The tube 1114 may extend from the flexible cable 1112 through the collar 1118. The collar 1118 may be designed to restrict the passage through which the tube 1114 passes. The tube 1114 may be attached to the collar 1118 using adhesive to fix the tube to the collar 1118 thereby fixing the position of the tube 114 to the flexible cable 1112.

Figure 13:
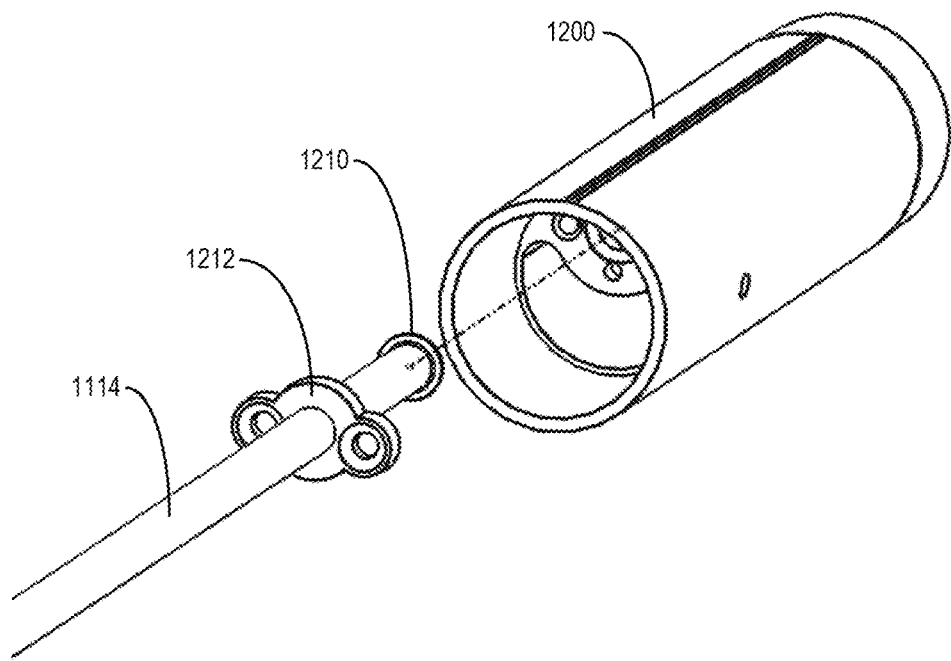
FIG. 13 is an assembly view of the tube being attached to the imager head.

FIG. 13 is an assembly view of the tube 1114 being attached to the imager head 1200. The tube 1114 may have a lip 1210. The lip 1210 may be a larger diameter than the main portion of the tube 1114 extending through the flexible cable 1112. A collar 1212 may be fastened to the imager housing 1200, for example using screws or bolts. The collar 1212 may trap the lip 1210 against a surface of the imager housing 1200 to fix the tube to the imager housing 1200. By fixing the tube 1114 against the imager housing 1200, the tube 1114 may be fixed relative to the flexible 1112.

Figure 14A:
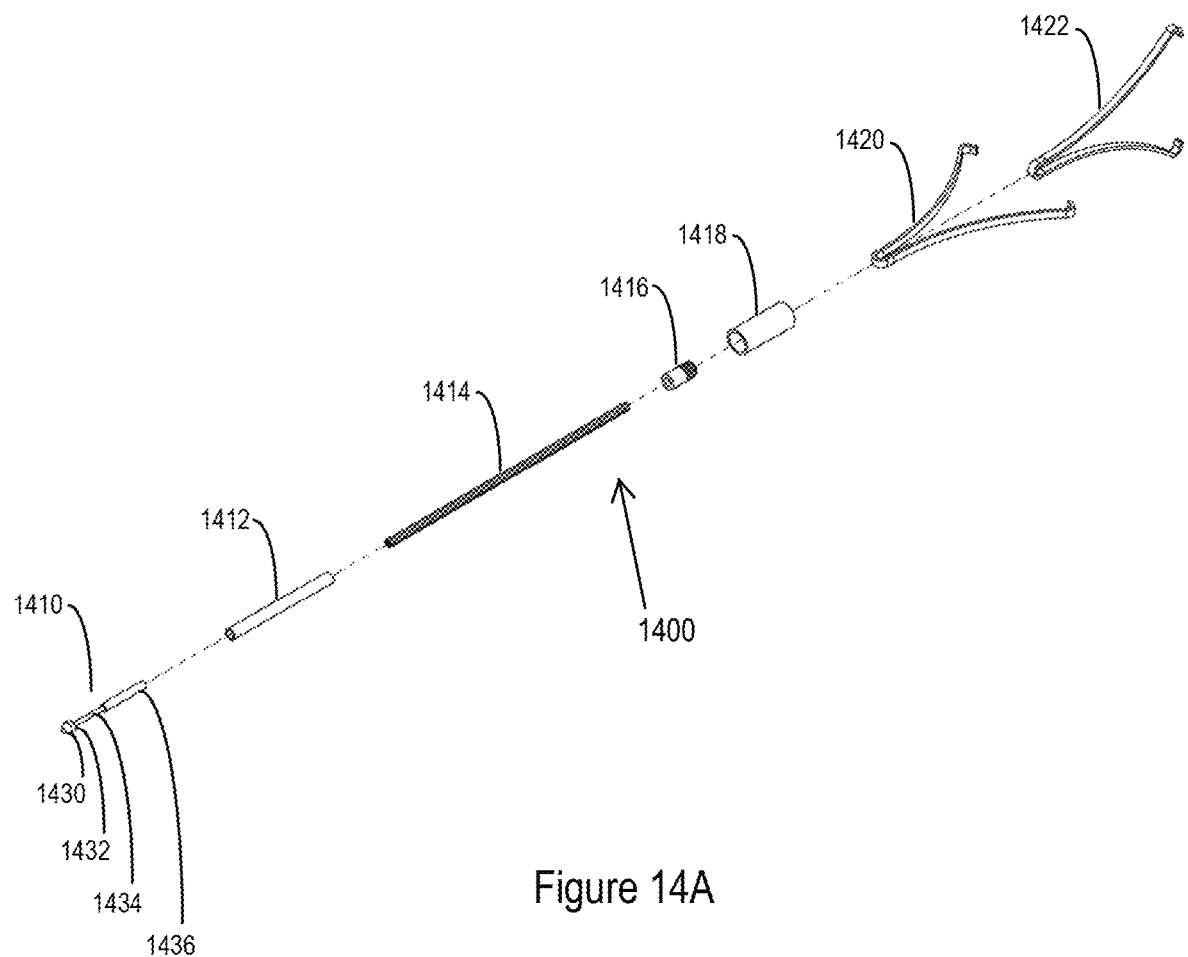
FIG. 14A is an exploded view of one implementation of a grasper.
Figure 14B:
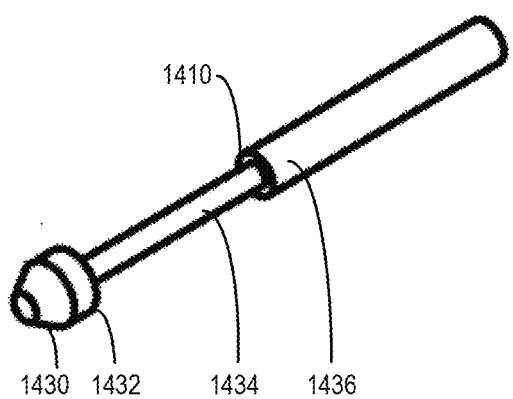
FIG. 14B is a perspective view of the proximal end of the grasper.

FIG. 14A is an exploded view of one implementation of a grasper 1400 and FIG. 14B is a perspective view of the proximal end portion 1410 of the grasper 1400. The grasper 1400 may include a proximal end portion 1410. The proximal end portion 1410 may include a conical shape 1430. The conical end portion 1430 may have a rounded tip. The conical shape 1430 may have a cylindrical extension 1432 on the base of the conical shape 1430. The conical shape 1430 may have a surface angle of between 30 and 60 degrees with a vertex of the conical shape 1430. The proximal end 1410 may have a reduced diameter section 1434 extending between the conical shape 1430 and a grasper cable 1414, the grasper cable 1414 extending from the proximal end 1410 of the grasper 1400 toward the imager housing. The reduced diameter section 1434 may extend through a slot in a retention mechanism attached to the actuating mechanism such that the retention mechanism engages the proximal end 1410. The proximal end 1410 may have an end portion 1436 attached to a fastening tube 1412. The end portion 1436 may extend into the opening in the fastening tube 1412. The end portion 1436 may be threaded and engage the fastening tube 1412 through the threads. Although, the end portion 1436 may be attached to the fastening tube 1412 through other means such as adhesive, crimping, or other methods. The grasper cable 1414 may extend into an opposite opening in the fastening tube 1412. The fastening tube 1412 may engage the grasper cable 1414 through various means, for example adhesive, crimping, or other methods.

The grasper cable 1414 is not shown to length. The opposite end of the grasper cable 1414 may be fastened to a second fastening tube 1416. The grasper cable 1414 may extend into the second fastening tube 1416 and may be attached by various means, for example adhesive or crimping. The second fastening tube 1416 may be threaded and engage the tine connector 1418 through the threads. The tine connector 1418 may receive horizontal tines 1420 and vertical tines 1422. The horizontal tines 1420 and vertical tines 1422 may be received within the tine connector 1418 and may be attached to the tine connector 1418 through various means for example adhesive, crimping, press fit, or other methods.

Figure 15A:
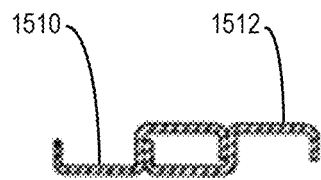
FIGS. 15A, B, and C are cross sectional views of one implementation of a flexible cable.

FIGS. 15A, B, and C are cross sectional views of one implementation of a flexible cable as discussed elsewhere in this application. The wall of a flexible cable may be made of overlapping segments for example segment 1510 and segment 1512. FIG. 15A illustrates where the overlapping segments are compressed. The segments may be compressed for example at the inside of a bend. In the compressed state, the outer edge of the first segment 1510 is pushed against an inner edge of the second segment 1512. Accordingly, the first segment 1510 overlaps the second segment 1512 to the maximum extent.

Figure 15B:
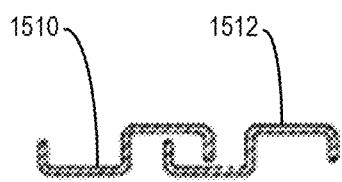
Figure 15C:
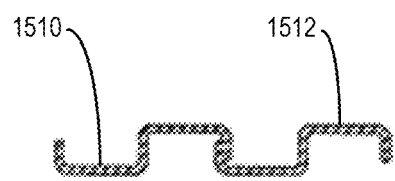

FIG. 15B illustrates the wall of the flexible cable in a neutral position. In the neutral position the first segment 1510 overlaps the second segment 1512 by an amount approximately halfway between the maximum and minimum extent. FIG. 15C illustrates the wall of the flexible cable in the expanded state. The segments may be expanded for example at the outside of a bend. In the expanded state, the outer edge of the first segment 1510 is pushed against an outer edge of the second segment 1512. Accordingly, the first segment 1510 overlaps the second segment 1512 to the minimum extent.

Figure 16:
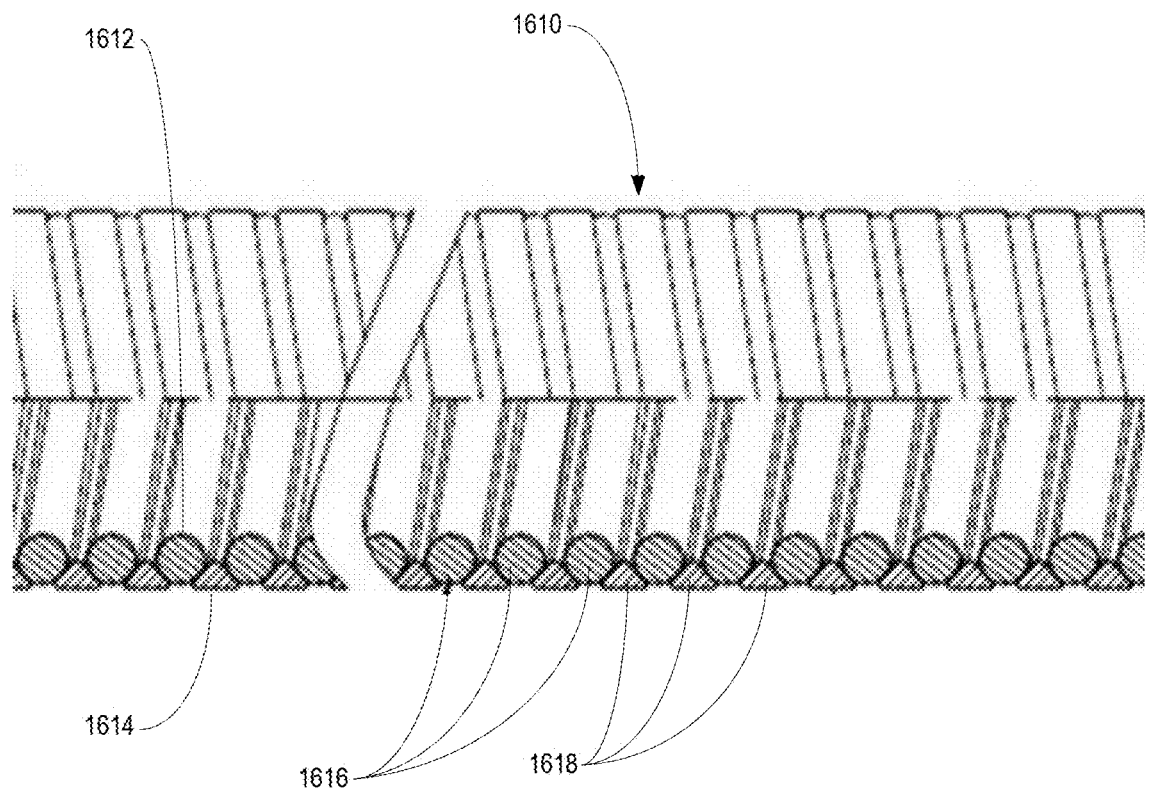
FIG. 16 is a partial cross sectional view of one implementation of flexible cable with a double wall construction.

FIG. 16 is a partial cross sectional view of one implementation of flexible cable as discussed elsewhere in this application with a double wall construction. The double wall provides benefits with respect to keeping alignment of the flexible cable 1610 with respect to the tube providing the internal passageway to the grasper cable. The double wall construction may include a first outer wall 1614 surrounding a second inner wall 1612. The inner wall 1612 of the flexible cable 1610 may engage the outer wall 1614 of the flexible cable 1610. Further, the inner wall 1612 of the flexible cable 1610 may engage the outer wall 1614 along at least 50% of the length of the flexible cable 1610. Each of the inner and outer walls may be coils. The inner and outer walls may or may not be bonded together. In some implementations, the outer wall 1614 (e.g. outer coil 1618) may ride in the groove created by the inner wall 1612 (e.g. inner coil 1616). The engagement restricts movement to some extent, but also is beneficial in stopping the conduit from expanding or contracting as opposed to a single wall solution.

Figure 17A:
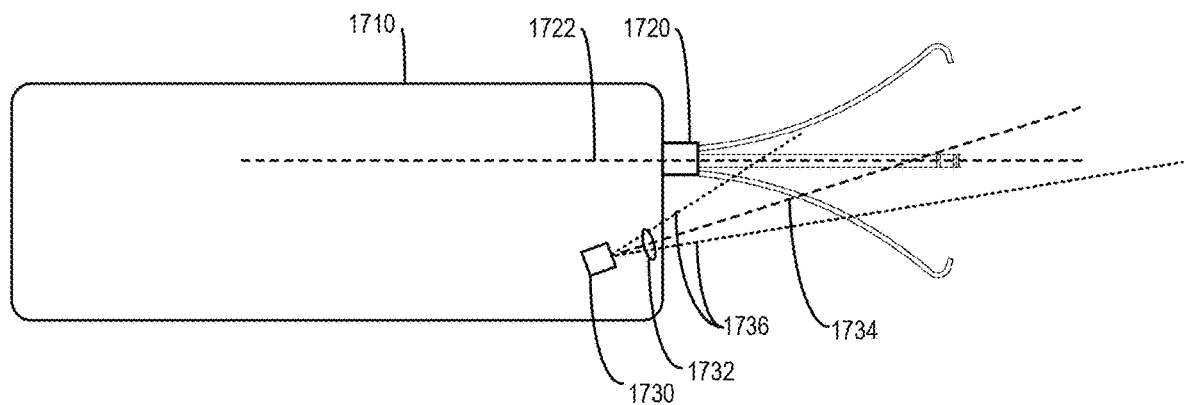
FIG. 17A and FIG. 17B are side views of the imager housing illustrating imaging and illumination configurations.

FIG. 17A is a side view of the imager housing 1710. The imager housing 1710 includes an imaging sensor 1730 and optics 1732. The imaging sensor 1730 and optics 1732 cooperate to create a field of view 1736 that may be acquired by the imaging sensor 1730. In some applications, it may be beneficial to view a particular area for example where the tines located when the grasper are fully extended to grasp an item. The grasper 1720 may extend from the imager housing 1710. The tines 1724 may open as the grasper 1720 is extended from the imager housing 1710. Accordingly, the center line 1734 of the field of view 1736 may intersect with the longitudinal axis 1722 of the grasper 1720. As such, the center line 1734 of the field of view 1736 may intersect with the longitudinal axis 1722 of the grasper 1720 between 15 mm and 35 mm from the end of the imager housing 1710. The center line 1734 may form an angle of between 10 and 20 degrees (for example, greater than 10 degrees) with the longitudinal axis of the grasper.

Figure 17B:
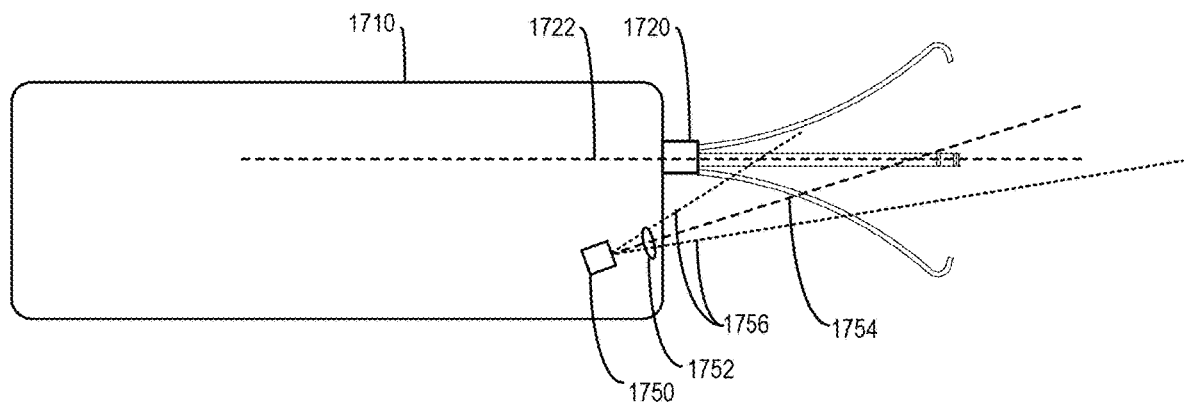

FIG. 17B is another side view of the imager housing 1710. The imager housing 1710 may also include a light source 1750 and optics 1752. The light source 1750 and optics 1752 cooperate to create a field of illumination 1756 that may be acquired by the light source 1750. In some applications, it may be beneficial to view a particular area for example where the tines located when the grasper are fully extended to grasp an item accordingly it may be beneficial to specifically illuminate that area. The grasper 1720 may extend from the imager housing 1710. The tines 1724 may open as the grasper 1720 is extended from the imager housing 1710. Accordingly, the center line 1754 of the field of illumination 1756 may intersect with the longitudinal axis 1722 of the grasper 1720. As such, the field of illumination 1756 may intersect with the longitudinal axis 1722 of the grasper 1720 between 1 mm and 30 mm from the end of the imager housing 1710. The center line 1754 may form an angle of between 0 and 45 degrees (for example, 10 degrees) with the longitudinal axis of the grasper.

As a person skilled in the art will readily appreciate, the above description is meant as an illustration of the principles of this disclosure. This description is not intended to limit the scope or application of this disclosure in that the disclosure is susceptible to modification, variation and change, without departing from spirit of this disclosure, as defined in the following claims.

What is claimed is:

1. A portable inspection unit comprising:
   a unit body;
   a flexible cable having a proximal end portion and a distal end portion, the proximal end portion extending from the unit body;
   an imager housing disposed at the distal end of the flexible cable;
   a tube extending from the unit body to the imager housing through the flexible cable, a proximal end of the tube being fixed to a proximal end of the flexible cable and a distal end of the tube being fixed to a distal end of the flexible cable
   a grasper having a grasper cable extending from the unit body to the imager housing through the tube, the grasper being attached to an actuating unit in the unit body to extend and retract the grasper from a distal end of the imager housing; and
   a retaining mechanism in the unit body configured to engage a feature on a proximal end of the grasper cable, the retaining mechanism having a sloped front surface and a sloped back surface, the sloped font surface oriented such that the feature on the grasper cable rides up the sloped front face as the grasper cable is fed proximally, the back surface being sloped relative to the central axis of the grasper cable, wherein the retaining mechanism has a slot aligned with central axis of the grasper cable and extending from the sloped front surface to the back surface and sized to receive the grasper cable therein.

2. The portable inspection unit of claim 1, wherein the proximal end of the tube is fixed to the unit body and the unit body is fixed to the proximal end of the flexible cable.

3. The portable inspection unit of claim 1, wherein the proximal end of the tube is fixed to the unit body through a collar.

4. The portable inspection unit of claim 1, wherein the distal end of the tube is fixed to the imager head and the imager head is fixed to the proximal end of the flexible cable.

5. The portable inspection unit of claim 1, wherein the distal end of the tube is fixed to the imager head through a clamp.

6. The portable inspection unit of claim 1, wherein the grasper comprises a plurality of tines.

7. A portable inspection unit comprising:
   a unit body;
   a flexible cable having a proximal end portion and a distal end portion, the proximal end portion extending from the unit body;
   an imager housing disposed at the distal end of the flexible cable;
   a grasper having a grasper cable and a plurality of tines, the grasper extending from the unit body to the imager housing through the flexible cable; and
   a retaining mechanism in the unit body configured to engage a feature on a proximal end of the grasper cable;
   wherein the retaining mechanism has a sloped front surface oriented such that the feature on the grasper cable rides up the sloped front face as the grasper cable is fed proximally, and wherein the retaining mechanism has a slot aligned with central axis of the grasper cable and extending from the sloped front surface to a back surface of the retaining mechanism, the feature having a width greater than a width of the slot, the back surface being sloped relative to the central axis of the grasper cable.

8. The portable inspection unit of claim 7, wherein the feature has a width greater than a width of the grasper cable.

9. The portable inspection unit of claim 7, further comprising a lever that engages the feature of the grasper cable.

10. The portable inspection unit of claim 9, wherein the lever has a first arm configured to be depressed to release engagement of the feature from the retaining mechanism.

11. A portable inspection unit comprising:
    a unit body;
    a flexible cable having a proximal end portion and a distal end portion, the proximal end portion extending from the unit body;
    an imager housing disposed at the distal end of the flexible cable; and
    a grasper extending from the unit body to the imager housing, a proximal end of the grasper being attached to an actuating unit in the unit body to extend and retract the grasper from a distal end of the imager housing, the proximal end of the grasper having a conical shape;
    wherein the proximal end has a reduced diameter section extending between the conical shape and a grasper cable, the grasper cable extending from the proximal end of the grasper toward the imager housing, wherein the reduced diameter section extends through a slot in a retention mechanism attached to the actuating unit such that the retention mechanism engages the proximal end.

12. The portable inspection unit of claim 11, wherein the conical shape has a rounded tip.

13. The portable inspection unit of claim 11, wherein the conical shape has a surface angle of between 30 and 60 degrees with a vertex of the conical shape.

14. The portable inspection unit of claim 11, wherein the conical shape has a cylindrical extension on a base of the conical shape.

* * * * *